(12) United States Patent
Smith et al.

(10) Patent No.: US 11,638,648 B2
(45) Date of Patent: May 2, 2023

(54) WRIST ARTHROPLASTY SYSTEM AND METHOD

(71) Applicant: Acumed LLC, Hillsboro, OR (US)

(72) Inventors: Terrence Chadwick Smith, Portland, OR (US); Bryon Marshall Morse, Lake Oswego, OR (US); Mark Bernhard Sommers, Beaverton, OR (US); Charles Andrew Pailthorpe, Reading (GB)

(73) Assignee: Acumed LLC, Hillsboro, OR (US)

( * ) Notice: Subject to any disclaimer, the term of this patent is extended or adjusted under 35 U.S.C. 154(b) by 192 days.

(21) Appl. No.: 17/152,268

(22) Filed: Jan. 19, 2021

(65) Prior Publication Data

US 2021/0220144 A1 Jul. 22, 2021

Related U.S. Application Data

(60) Provisional application No. 62/964,400, filed on Jan. 22, 2020.

(51) Int. Cl.
*A61F 2/42* (2006.01)
*A61F 2/46* (2006.01)

(52) U.S. Cl.
CPC .......... *A61F 2/4261* (2013.01); *A61F 2/4657* (2013.01); *A61F 2/4684* (2013.01); *A61F 2002/4282* (2013.01); *A61F 2002/4662* (2013.01); *A61F 2310/00023* (2013.01); *A61F 2310/00029* (2013.01)

(58) Field of Classification Search
CPC ...... A61F 2002/4282; A61F 2002/4264; A61F 2/4261; A61F 2002/4662; A61F 2/4657; A61B 17/1782
See application file for complete search history.

(56) References Cited

U.S. PATENT DOCUMENTS

| 2009/0198244 A1* | 8/2009 | Leibel | A61B 17/1782 |
| | | | 606/87 |
| 2013/0331947 A1* | 12/2013 | Surma | A61B 17/1725 |
| | | | 606/99 |

FOREIGN PATENT DOCUMENTS

| EP | 2559407 A2 * | 2/2013 | ......... A61B 17/1739 |
| WO | WO-2016149764 A1 * | 9/2016 | ......... A61B 17/1746 |

* cited by examiner

*Primary Examiner* — Javier G Blanco
(74) *Attorney, Agent, or Firm* — K&L Gates LLP (57) ABSTRACT

The present disclosure provides for a wrist arthroplasty system and method that enable an expedient surgical procedure, maintain wrist motion, and reduce the likelihood of implant loosening. The system includes a capitate implant, a radial implant, and a resection instrument. The capitate implant includes a convex head formed to interface with a concave socket of the radial implant. The capitate implant includes a single stem formed to be secured within a patient's capitate bone. The radial implant includes lips formed to increase wrist joint motion and to help prevent dislocation of the capitate implant from the radial implant. The resection instrument may be used in combination as a measurement tool for determining the proper implant size, a guide for properly positioning the implants, and a trial tool for testing trial implant components before securing the final radial and capitate implants.

9 Claims, 7 Drawing Sheets

WRIST ARTHROPLASTY SYSTEM AND METHOD

PRIORITY CLAIM

The present application claims priority to and the benefit of U.S. Provisional Application 62/964,400, filed Jan. 22, 2020, the entirety of which is herein incorporated by reference.

BACKGROUND

Patients sometimes experience pain or limited range of motion with or deformity of one or both of their wrists. Such pain and motion limitations may be caused by a variety of factors. For example, patients may have a non-inflammatory degenerative joint disease such as osteoarthritis, traumatic arthritis, and/or avascular necrosis. Patients may also have rheumatoid arthritis or a functional deformity such as Scapholunate Advanced Collapse (SLAC). In other instances, patients may experience a trauma to one or both wrists, including fractures of the distal radius and/or carpal bones. Regardless of the cause, in some cases, the pain, limited range of motion, or damage to a patient's wrist may necessitate surgical procedures on the wrist. Typical procedures include proximal row carpectomies, wrist fusions, and/or total wrist joint replacements with an artificial joint. A proximal row carpectomy is a procedure that excises the scaphoid, lunate, and triquetrum bones of the wrist joint. Wrist fusions leave a patient with a very limited wrist function. Similarly, a failed or degenerating proximal row carpectomy often leads to a wrist fusion, and thus very limited wrist function. Accordingly, artificial wrist joints may help patients relieve pain and maintain functional range of motion of the wrist.

The wrist/radiocarpal joint is an ellipsoid type of synovial joint. The wrist consists of two rows of carpal bones which form the proximal segment of the hand and articulate proximally with the forearm via the wrist joint and distally with the five metacarpals of the fingers. The forearm includes the radius and ulna bones. The row of carpal bones nearest the forearm include the scaphoid, lunate, and triquetrum bones. The row of carpal bones nearest the fingers include the trapezium, the trapezoid, the capitate, the hamate, and the pisiform bones. The ends of the bones are covered with articular cartilage, which is an elastic connective tissue that allows for a smooth, gliding motion between joints. Diseases such as osteoarthritis and rheumatoid arthritis, injury and infection, however, can damage or wear out the articular cartilage causing the wrist bones to rub against each other producing pain, stiffness, and/or swelling of the wrist.

SUMMARY

The present disclosure provides new and innovative systems and methods for performing a wrist arthroplasty. In an example, a system includes a capitate implant, a radial implant, and a resection instrument. The capitate implant includes a capitate stem extending from a carpal surface of a head portion. The head portion includes a convex surface opposite the carpal surface. The radial implant includes a radial stem extending from a first side of a base component and a socket extending from a second side of the base component opposite the first side. The socket includes two lips forming a concave opening adapted to interface with the convex surface of the capitate implant. The resection instrument includes a distal radius guide, a guide block, and a depth control instrument. The distal radius guide includes a trial socket formed integrally with a reaming guide, and the trial socket is configured to substantially replicate the socket of the radial implant. The reaming guide includes an opening sized according to the trial socket. The guide block includes a plurality of holes each adapted respectively to receive a fixture instrument, and the guide block is configured to receive the depth control instrument. The depth control instrument includes an adjustment knob, and is configured to removably engage with the guide block such that, when engaged, rotating the adjustment knob causes the depth control instrument to translate relative to the guide block.

In an example, a method uses a resection instrument including a set of interchangeable distal radius guides, a guide block, and a depth control instrument, and each respective distal radius guide of the set of interchangeable distal radius guides includes a trial socket formed integrally with a reaming guide. The method includes creating an incision relative to the wrist and excising, respectively, each of a scaphoid bone, a lunate bone, and a triquetrum bone. The method then includes selecting a respective distal radius guide from the set of interchangeable distal radius guides for use with the resection instrument based on a radius bone. The respective distal radius guide includes a respective trial socket and a respective reaming guide. The guide block is then removably secured to the radius bone and a distal surface of the radius bone is prepared with the aid of the respective reaming guide while the guide block is removably secured to the radius bone. A capitate implant is then aligned based on the respective trial socket while the guide block is removably secured to the radius bone. The method then includes securing the capitate implant to a capitate bone such that a capitate stem of the capitate implant is inserted within a capitate hole created in the capitate bone. The radial implant is then aligned according to alignment marks on the guide block removably secured to the radius bone, and secured to the radius bone such that a radial stem of the radial implant is inserted within a radial hole created in the radius bone. The guide block is then removed from the radius bone.

DETAILED DESCRIPTION

A wrist arthroplasty is a surgical procedure to restore the function of a patient's wrist joint by replacing the damaged joint with an artificial joint. Typically, an artificial wrist joint includes one or two components—a radial implant and/or a carpal implant. A wrist arthroplasty may be: 1) a total wrist arthroplasty in which both the radial implant and the carpal implant are used; or 2) a hemiarthroplasty in which only one of the radial implant or the carpal implant are used. The radial implant may include a cup or socket and the carpal implant may include a head with a convex surface that fits within the socket of the radial implant.

Common failure modes of typical wrist arthroplasty devices include implant loosening. Artificial wrist joints are not weight bearing joints, and thus physical demands placed on an artificial wrist joint, such as lifting heavy weights or repetitive movements, may increase the incidence of the implants loosening thereby causing ultimate failure of the artificial joint. The cause of loosening may be due to improper loading of the implant and to the implant being fixed in intramedullary canals rather than the cortical and subchondral layer of the native bone.

Some artificial wrist joints include a capitate implant with multiple stems that extend into multiple carpal bones to secure the capitate implant to the carpal bones. Other artificial wrist joints additionally have one or more of the stems extend into the metacarpals. Both of these approaches lead to over-constraining of the wrist by preventing intercarpal motion, which further facilitates loosening of the implants. For example, by anchoring the capitate implant to two or more separate carpal bones, motion of those respective carpal bones relative to one another is restricted. For instance, a certain wrist motion may require a first carpal bone housing a stem to move a first direction and a second carpal bone housing a stem to move a second, opposite direction. However, the stems prevent the respective carpal bones from moving in the corresponding direction. Likewise, if a stem extends into a metacarpal, motion of the respective metacarpal relative to the other carpals and metacarpals is restricted. Accordingly, wrist motion is restricted.

Additionally, the restricted wrist motion causes two or more carpal bones to place competing forces on the implant each time patients move their hand. The competing forces of two or more carpal bones moving in opposite directions causes stress to be placed at the interface between the implant stems and the bones housing the stems, or the material (e.g., bone cement) securing the stem to the bone. Over time (e.g., 10 years), the repetitive stress may cause the capitate implant to loosen from the carpal bones that the stems are within. For instance, cement securing the implant stem to a hole created in a carpal bone may fail. Further facilitating the loosening of the implants is the typical method of excessively resecting the end of each of the distal radius bone and the proximal capitate bone prior to securing the implants to their respective bones. Excessively resecting the end of each bone causes the above-described stresses to be placed mainly on the stems within the intramedullary canals of each bone, and increases the likelihood that the stems will loosen from within the canals. Loosening of the implants may cause wrist pain and may require replacement of the implants or an alternative treatment option.

To solve these technical problems, among others, the present disclosure provides a wrist arthroplasty system and method that enables an expedient surgical procedure, maintains wrist motion, and reduces the likelihood of implant loosening as compared to typical wrist arthroplasty systems. The provided system includes a capitate implant with a single stem that is secured in a hole created in a capitate carpal bone after excising the scaphoid, lunate, and triquetrum bones. By securing the capitate implant with a single stem in a single carpal bone, motion between the carpal bones is maintained and the likelihood that the capitate implant will loosen is reduced. For example, each of the carpal bones may move freely relative to one another. Additionally, the carpal bones are not restricted by the capitate implant, and thus there are no competing forces to generate material stress as described above. The likelihood of implant loosening is further reduced by resurfacing the proximal capitate bone and the distal radius bone such that the subchondral bone of each surface is preserved at the loading points for each respective implant (e.g., the capitate implant and the radial implant described below, respectively).

In at least some aspects, the provided system also includes a radial implant with a socket that includes lips. The lips may help increase wrist joint motion by better maintaining the capitate implant head within the socket. The lips may also help prevent dislocation of the capitate implant from the radial implant.

In at least some aspects, the provided system includes a resection instrument for use in the surgical procedure of inserting the radial and capitate implants. The provided resection instrument may be used as a measurement tool for determining the proper implant size, a guide for properly positioning the implants, and a trial tool for testing trial implant components before fixedly securing the final radial and capitate implants. The resection instrument may also control reaming depth, and may have its alignment fixed during reaming, to ensure preservation of the subchondral bone of each of the radius bone and the capitate bone. Accordingly, the resection instrument may help enable expedient and consistent surgical procedures by allowing each step of the procedure to be performed with a single instrument that maintains consistent alignment throughout the procedural steps.

Figure 1A:
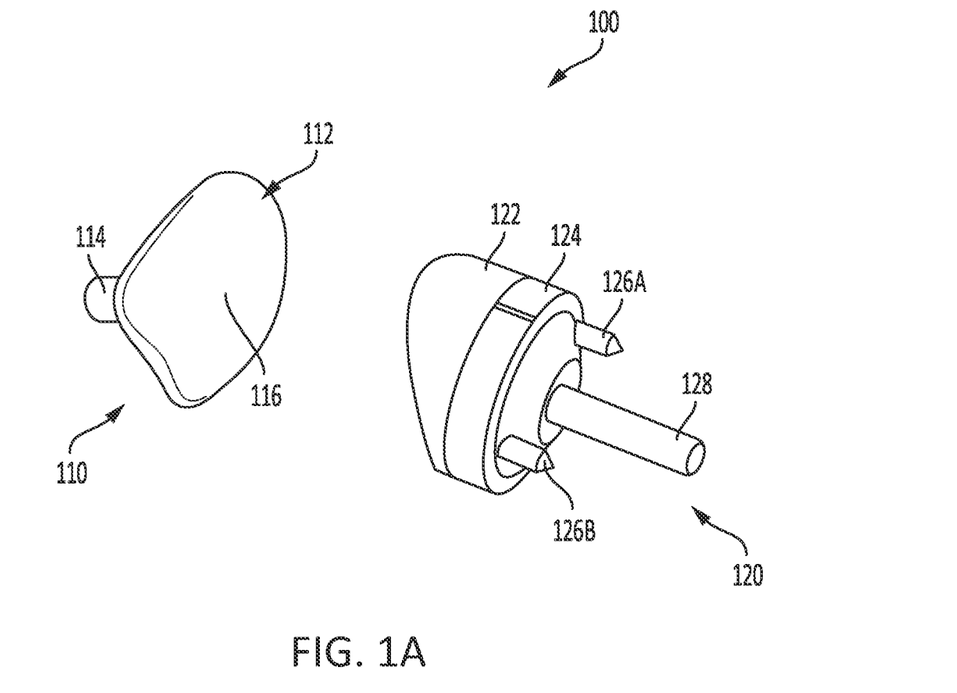
FIG. 1A illustrates a perspective view of an example artificial wrist joint, according to an aspect of the present disclosure.
Figure 1B:
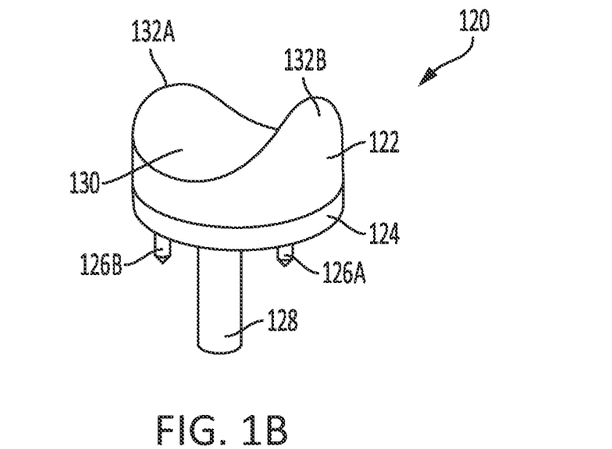
FIG. 1B illustrates an isometric view of an example radial implant, according to an aspect of the present disclosure.
Figure 1C:
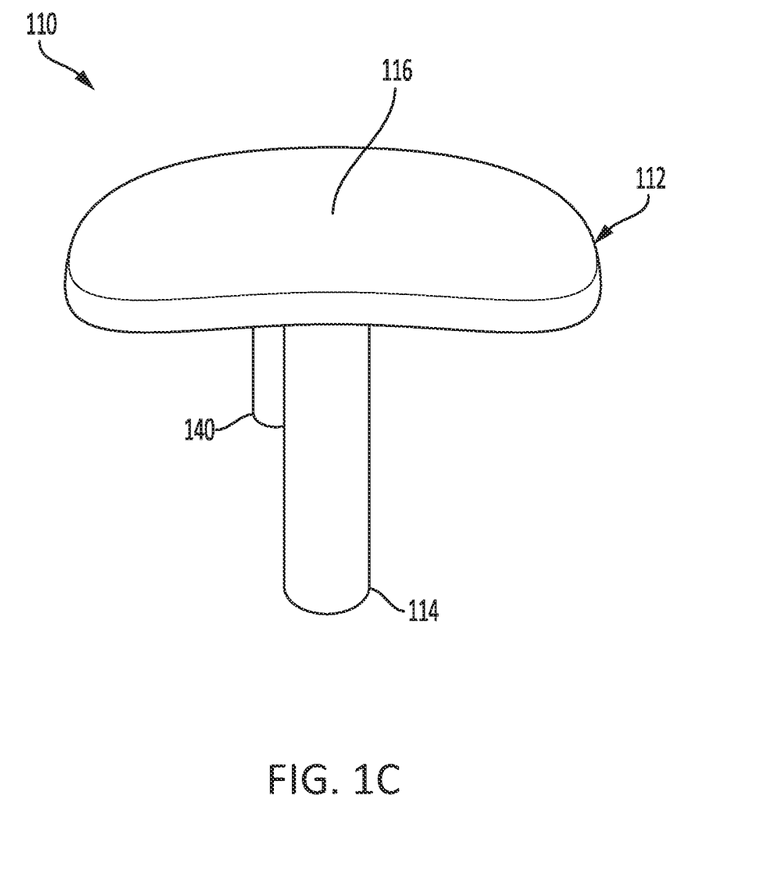
FIG. 1C illustrates an isometric view of an example capitate implant, according to an aspect of the present disclosure.

FIG. 1A illustrates a perspective view of an example artificial wrist joint 100, according to an aspect of the present disclosure. In various aspects, the example artificial wrist joint 100 includes a capitate implant 110 and a radial implant 120. In some aspects, the example capitate implant 110 or the example radial implant 120 may be used individually. The capitate implant 110 may include a stem 114 extending from a carpal surface of a head 112. In some aspects, the stem 114 may be formed integrally with the head 112. In other aspects, the stem 114 may be a separate component that is attached to the head portion 112. The stem 114 may, in various examples, include a protrusion 140 extending out from the stem 114 along at least a portion of the length of the stem 114. FIG. 1C illustrates an isometric view of an example capitate implant 110 with a protrusion 140 extending along a portion of the stem 114 of the capitate implant 110, according to an aspect of the present disclosure. In other examples, the protrusion 140 may extend along the entire length of the stem 114, or any other portion of the length of the stem 114. The protrusion 140 may be used to secure the capitate implant 110 in place by preventing the capitate implant 110 from rotating, as will be described in more detail below. The head 112 also includes a convex surface 116.

In various aspects, the convex surface 116 may be configured with a curvature that replicates a surface of a lunate carpal bone. For instance, as will be described in more detail below, the provided method includes excising the proximal carpal row including the lunate carpal bone and inserting the stem 114 of the capitate implant 110 within a hole created in a capitate bone. Thus, the capitate implant 110 may be configured to simulate the lunate bone by having a convex surface 116 that replicates the curvature of a lunate bone's surface that natively interfaces with the radius bone. Configuring the convex surface 116 to replicate the lunate bone surface instead of the capitate bone surface ensures a congruous joint interface between the distal and radial implants to avoid low surface contact. Low surface contact can cause high pressure stress areas and thus should be avoided. Additionally, the configuration of the convex surface 116 to replicate the lunate surface enables the capitate implant 110 to be used in a total wrist arthroplasty procedure and a hemiarthroplasty procedure. Stated differently, the convex surface 116 may interface with a radial implant 120 or with a radius bone itself given that it replicates a lunate bone surface which natively interfaces with the radius bone.

In some aspects, the capitate implant 110 is composed entirely of one or more metals, such as a cobalt chromium alloy. In other aspects, the capitate implant 110 may include other medical-grade, biologically-suitable materials. In some aspects the stem 114 of the capitate implant 110 is sprayed with a titanium plasma to help facilitate bony ongrowth. For instance, the bony ongrowth on the stem 114 may help to secure the stem 114 to the bone hole that the stem 114 is inserted within, and thus the capitate implant 110 to the respective bone, such as the capitate bone.

In at least some aspects, the radial implant 120 includes a stem 128 extending from a first side of a base component 124 and a socket 122 extending from the other side of the base component 124. In some examples, the radial implant 120 may include posts 126A, 126B extending from the same side of the base component 124 as the stem 128. The posts 126A, 126B may help prevent the radial implant 120 from rotating when the stem 128 and the posts 126A, 126B are inserted within a bone. FIG. 1B illustrates a top perspective view of the radial implant 120, according to an aspect of the present disclosure. The illustrated example shows a concave opening 130 of the socket 122 of the radial implant 120. In some aspects, the socket 122 includes lips 132A and 132B that form the concave opening 130 to increase joint motion and prevent dislocation of the capitate implant 110 from the radial implant 120. For example, the capitate implant 110 may slide along the surface of the concave opening 130 and upward along either lip 132A, 132B while still remaining contained within the concave opening 130. Without the lips 132A and 132B, the capitate implant 110 could not slide as far before the interface between the capitate implant 110 and the concave opening 130 is lost and the capitate implant 110 dislocates from within the concave opening 130. Thus, patients may move their hands at their wrist joints to a greater degree without causing problems with a radial implant 120 that includes lips 132A, 132B than with a radial implant 120 that does not have lips 132A, 132B.

In some instances, the concave opening 130 may include the same radius of curvature forming the lip 132A as the radius of curvature forming the lip 132B. In other instances, the concave opening 130 may include a different radius of curvature forming the lip 132A than the radius of curvature forming the lip 132B. For example, as illustrated in FIG. 1B, the radius of curvature forming the lip 132B may be greater than the radius of curvature forming the lip 132A. In such examples, the lip 132B may extend higher (e.g., away from the base component 124) than the lip 132A.

In some aspects, the radial implant 120 may include a metal alloy, such as a titanium alloy. In other aspects, the radial implant 120 may include other medical-grade, biologically-suitable materials. In some examples, the radial implant 120 may be formed integrally as a single component. In such examples, the socket 122 may include a high molecular weight polyethylene liner on its surface. In other examples, the radial implant 120 may include two components: (1) the socket 122, and (2) a second component including the base component 124, the posts 126A, 126B, and the stem 128. The socket 122 may be configured to couple with the base component 124. For example, the socket 122 may snap into the base component 124. In such examples, the socket 122 may be composed of high molecular weight polyethylene. The base component 124, the posts 126A, 126B, and the stem 128 may be composed of a titanium alloy or other medical-grade, biologically suitable material in such examples.

Figure 2:
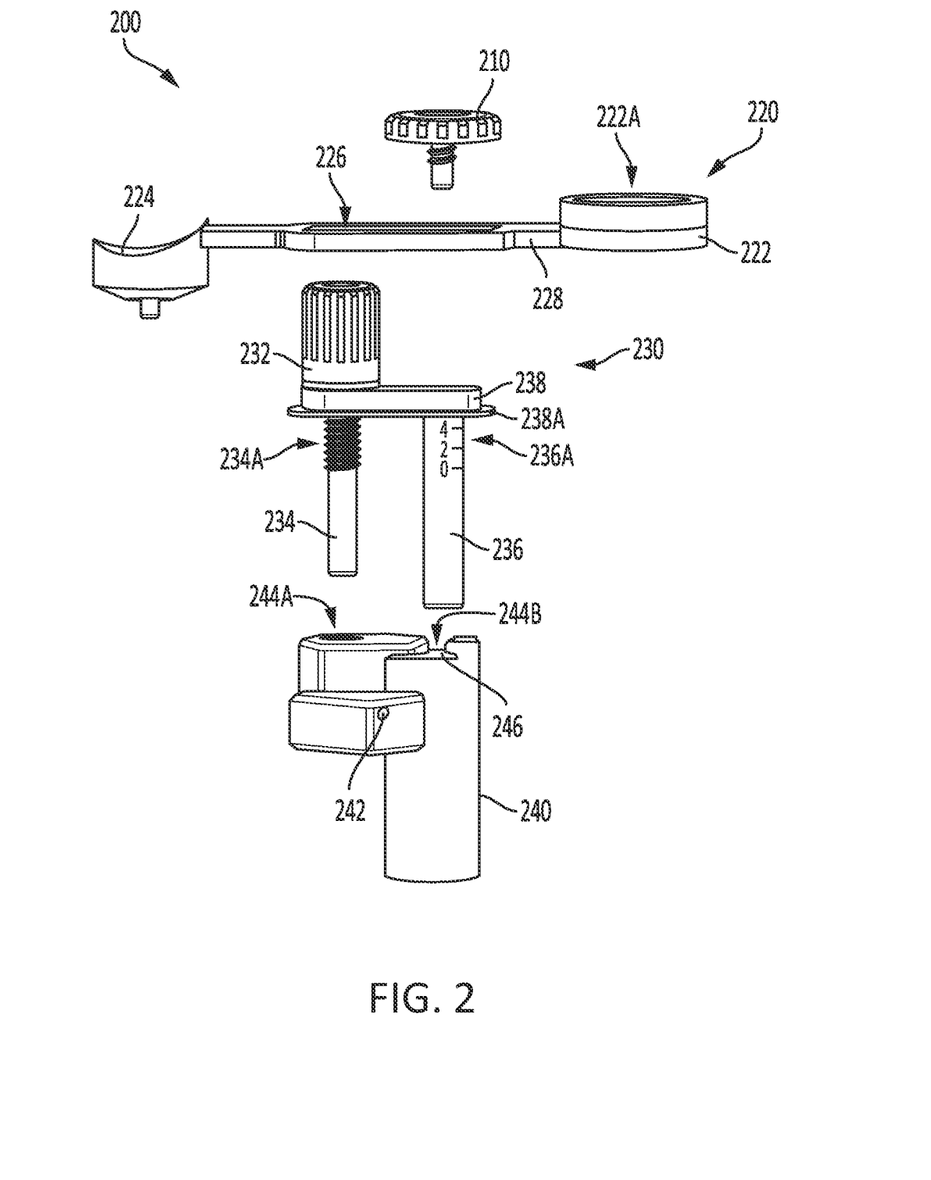
FIG. 2 illustrates an exploded view of an example resection instrument, according to an aspect of the present disclosure.

FIG. 2 illustrates an exploded view of an example resection instrument 200, according to an aspect of the present disclosure. The example resection instrument 200 includes a securing bolt 210, a distal radius guide 220, a depth control instrument 230, and a guide block 240. In some aspects, the guide block 240 is configured with one or more fixture openings 242 that enable a fixture instrument to secure the guide block 240 to another object. For example, the one or more fixture openings 242 may be configured for the insertion of k-wires to fix the guide block to a radius bone. In other examples, the guide block 240 may be adapted for use with other suitable fixture instruments (e.g. threaded wires, small screws, and clamps) to secure the guide block 240 to a radius bone.

In various aspects, the guide block 240 may be configured with the bores 244A, 244B to receive corresponding legs of the depth control instrument 230. For example, in some instances, the depth control instrument 230 may include a threaded leg 234 and an indicator leg 236, and the guide block 240 may correspondingly include the bore 244A adapted for the threaded leg 234 and the bore 244B adapted for the indicator leg 236. The bore 244A may be adapted for the threaded leg 234 by including a female threaded portion configured to removably engage with the threaded portion 234A of the threaded leg 234. The bore 244B may be adapted for the indicator leg 236 by enabling the indicator leg 236 to translate freely along the axis of the bore 244B. The indicator leg 236 includes an indicator portion 236A with multiple indicators (e.g., three indicators "4", "2", "0" as illustrated), and thus as the indicator leg 236 translates along the axis of the bore 244B some or all of the indicators may be visible outside of the bore 244B. In some instances, the guide block 240 may include a notch 246 such that the topmost indicator (e.g., indicator "4" as illustrated) is visible when the threaded portion 234A of the depth control instrument 230 is fully engaged with the female threaded portion of the guide block 240. In some instances, the guide block 240 may include one or more alignment marks (FIG. 4) for use in a wrist arthroplasty procedure, which will be described in more detail below.

In various aspects, the depth control instrument 230 includes a knob 232 formed integrally with the threaded leg 234 such that rotating the knob 232 also rotates the threaded leg 234. In other aspects, the knob 232 may be a separate component from the threaded leg 234 and may be connected to the threaded leg 234 such that rotating the knob 232 also rotates the threaded leg 234. In various aspects, the indicator leg 236 of the depth control instrument 230 is formed integrally with a base 238. In other aspects, the indicator leg 236 may be a separate component from the base 238 and may be connected to the base 238. The base 238 may include an opening (not illustrated) adapted to enable the knob 232 to rotate the threaded leg 234. When the threaded portion 234A of the depth control instrument 230 is engaged with the guide block 240, rotating the knob 232 causes the depth control instrument 230 to translate relative to the guide block 240. In other words, the threaded leg 234 and the indicator leg 236 may translate along the axes of their respective openings 244A, 244B in the guide block 240 as the knob 232 is rotated.

Although the depth control instrument 230 is described as having two legs, the threaded leg 234 and the indicator leg 236, in other examples, the depth control instrument 230 may have a single leg with a combined threaded portion and indicator portion. In such other examples, the guide block 240 may correspondingly have a single opening adapted for the single leg.

In various examples, the distal radius guide 220 may include a trial socket 224 formed integrally with a reaming guide 222 via a connecting portion 228. In other examples, one or all of the trial socket 224, the connecting portion 228, and the reaming guide 222 may be separate components that are connected. The connecting portion 228 may include an opening 226 sized corresponding to the base 238 of the depth control instrument 230 such that the outer perimeter of the opening 226 conforms to the outer perimeter of the base 238. Stated differently, the distal radius guide 220 is unable to rotate when secured on the base 238. Additionally, the base 238 and the opening 226 are configured such that the distal radius guide 220 may be oriented, for example, with the knob 232 nearest the trial socket 224 or with the knob 232 nearest the reaming guide 222. Such a configuration enables the distal radius guide 220 to be removed and rotated during an arthroplasty procedure, as will be described in more detail below.

Figure 3A:
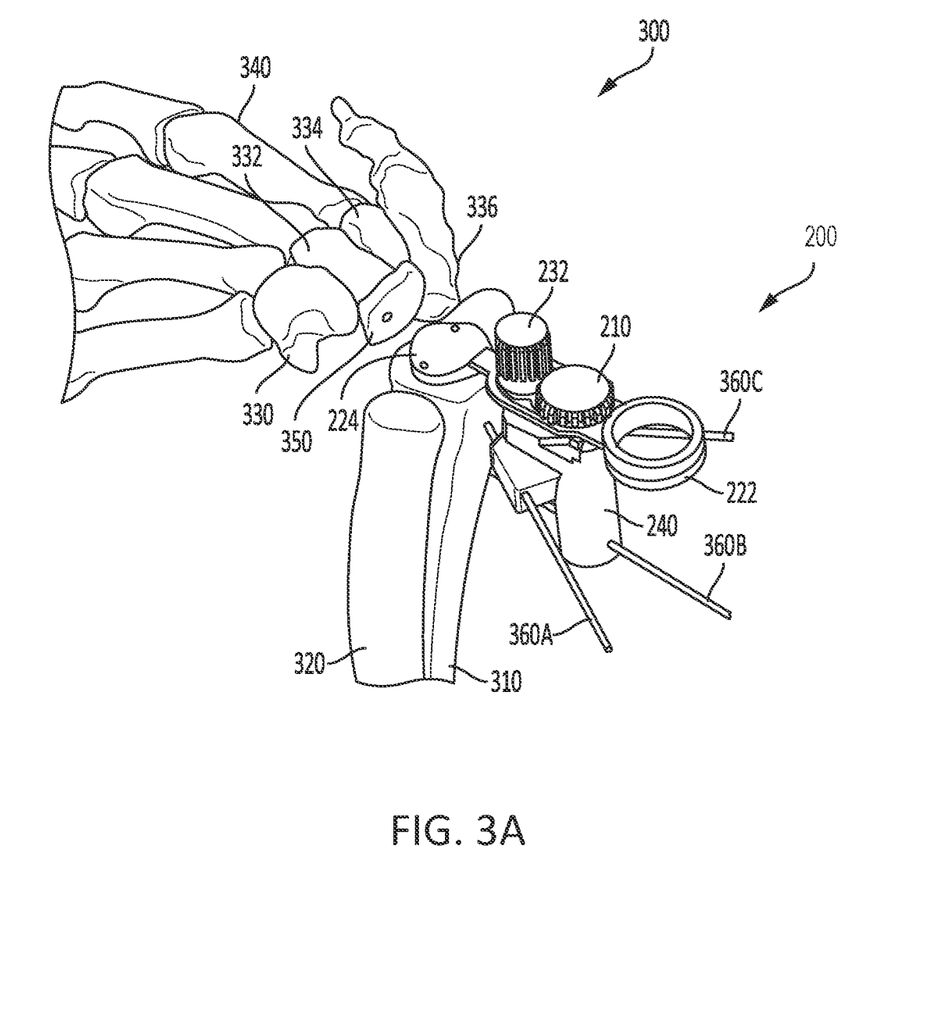
FIG. 3A illustrates a schematic of a patient including a resection instrument secured to a radius bone of the patient, according to an aspect of the present disclosure.

In some examples, the base 238 and the opening 226 may be configured such that the distal radius guide 220 cannot be secured to the depth control instrument 230 upside down. Stated differently, the distal radius guide 220 can only be positioned with respect to the base 238 such that the concave surface of the trial socket 224 faces away from the distal radius surface of the radius 310 (FIG. 3) when the resection instrument 200 is in use. For example, the opening 226 and the base 238 may have an axis symmetric irregular shape that allows the components to only fit with the correct side up.

In various aspects of the present disclosure, the base 238 of the depth control instrument 230 may include a lip 238A that may extend further than the outer perimeter of the opening 226 such that the distal radius guide 220 may rest on the lip 238A. The distal radius guide 220 may be removably secured to the depth control instrument 230. For example, the distal radius guide 220 may be removably secured with a bolt 210 wider than the opening 226 that screws into the depth control instrument 230 and prevents the distal radius guide 220 from being removed from the depth control instrument 230. The bolt 210, however, may be removed to allow the distal radius guide 220 to be removed from the depth control instrument 230 so that the distal radius guide 220 may be rotated and secured again to the depth control instrument 230, as will be described in more detail below.

Additionally, the distal radius guide 220 and the depth control instrument 230 are configured such that when the depth control instrument 230 translates relative to the guide block 240, the distal radius guide 220 translates with the depth control instrument 230. Accordingly, as the depth control instrument 230 translates away from the guide block 240, the distal radius guide 220 translates with the depth control instrument 230.

The trial socket 224 of the distal radius guide 220 is configured to substantially replicate the socket 122 of the radial implant 120. By substantially replicating the socket 122, the trial socket 224 may be tested with a trial capitate implant to determine the proper alignment of the capitate implant 110 and the radial implant 120, as will be described in more detail below. For example, the trial socket 224 may be sized with an outer perimeter, or radius, that matches the socket 122. The trial socket may also include a concave opening with a curvature that matches the curvature of the concave opening 130 of the socket 122. The trial socket 224 may include radial lips that replicate the lips 132A, 132B of the socket 122. In some instances, the trial socket 224 may have different radii of curvature forming the radial lips, as described above with regard to the socket 122.

The reaming guide 222 of the distal radius guide 220 includes an opening 222A configured to enable a reamer to pass through. For instance, the reaming guide 222 may be placed on a distal surface of a radius bone and a reamer may pass through the opening 222A to prepare the distal surface of the radius bone. The opening 222A guides and restricts the reamer to preparing only the distal surface of the radius bone that is within the opening 222A, which is beneficial because no more reaming than necessary is performed on the radius bone. Accordingly, because the trial socket 224 is configured to substantially replicate the socket 122 of the radial implant 120, the opening 222A is sized according to the trial socket 224 so that a proper amount of the radius bone's distal surface is prepared (e.g., reamed) for the radial implant 120. Thus, the perimeter of the opening 222A may be equal to the outer perimeter of the trial socket 224.

In various aspects of the present disclosure, the provided system may include a set of distal radius guides (e.g., three) that each have different respective sizes. For example, a set of distal radius guides may include a distal radius guide having a trial socket with a 15 mm diameter, a distal radius guide having a trial socket with a 17 mm diameter, and a distal radius guide having a trial socket with a 19 mm diameter. The reaming guide of each respective distal radius guide is sized accordingly. In other examples, the set of distal radius guides may include more or less than three differently-sized guides (e.g., 2, 4, 7, 10, etc.). The various sizes of distal radius guides account for the varying sizes of patients that require a wrist arthroplasty.

In some aspects of the present disclosure, the provided system may include a set of reamers sized according to the set of distal radius guides in the system. For instance, each reamer in the set may correspond to a specific reaming guide of the set of distal radius guides. A reamer sized properly for the reaming guide enables optimal reaming of the radius bone's distal surface.

The present disclosure additionally provides for an example wrist arthroplasty method using the provided resection instrument. Although the method is presented in the order of steps described below, it will be appreciated that many other methods of performing the acts associated with the method may be used. For example, the order of some of the steps may be changed, certain steps may be combined with other steps, and some of the steps described are optional.

The example method may include creating an incision relative to the wrist. For example, a longitudinal, dorsal, midline incision may be made as it provides suitable access to the wrist and allows the example resection instrument to be secured close to the radius bone. In some instances, the incision is a minimum of 4.5 cm in length proximal to the dorsal end of the distal radius bone. The example method may then include performing a proximal row carpectomy by excising, respectively, each of a scaphoid bone, a lunate bone, and a triquetrum bone. The proximal surface of the capitate bone may then be prepared. To prepare the capitate bone's proximal surface, the patient's wrist may be positioned in flexion and a k-wire guide may be positioned over the patient's third metacarpal. A surgeon may then drill a k-wire into the patient's capitate bone, ensuring that the k-wire is centered in both the posterior-anterior and lateral planes. The k-wire guide may then be removed. A surgeon may then use a reamer to remove cartilage on the capitate bone until subchondral bone is reached to ensure preservation of the subchondral bone. After the capitate surface is prepared, a hole may be created in the capitate bone (e.g., with a drill). For example, the hole created may correspond to the stem 114 of the capitate implant 110 selected for the wrist arthroplasty.

The example method may then include selecting, based on a radius bone, a respective distal radius guide 220 from a set of interchangeable distal radius guides for use with the resection instrument 200. In an example, the set may include three different-sized distal radius guides—15 mm, 17 mm, and 19 mm—as described above. Selecting which distal radius guide in the set to use may include testing each distal radius guide to determine the largest trial socket size that does not extend past the dorsal or volar rims of the distal radius bone when the distal radius guide is properly positioned for testing. A distal radius guide 200 is properly positioned for testing when its trial socket 224 contacts the distal radius bone surface with the trial socket's concave surface facing away from the radius bone, and the axis along the longest length of the distal radius guide 220 is perpendicular to the dorsal rim of the radius bone. For example, a surgeon may properly position the 15 mm distal radius guide and find that the outer perimeter of the trial socket remains within outer rims of the distal surface of the radius bone, in other words, within the dorsal and volar rims. The surgeon may then properly position the 17 mm distal radius guide and find that the outer perimeter of the trial socket also remains within the dorsal and volar rims. The surgeon may then properly position the 19 mm distal radius guide and find that the outer perimeter of the trial socket extends beyond the dorsal rim. Accordingly, the 17 mm distal radius guide is the largest trial socket size possible and is selected for use with the resection instrument 200.

After selecting the distal radius guide 220 and assembling the resection instrument 200, a surgeon may create a hole in the radius bone. For example, the hole created may correspond to the stem 128 of the radial implant 120 selected for the wrist arthroplasty. The surgeon may then removably secure the guide block 240 of the resection instrument 200 to the radius bone. FIG. 3A illustrates a schematic of a patient 300 including an example resection instrument 200 secured to a radius bone 310 of the patient 300, according to an aspect of the present disclosure. Also illustrated for context are the ulna bone 320, the hamate bone 330, the capitate bone 332, the trapezoid bone 334, the trapezium 336, and the five metacarpals 340 (only one of which is labeled) of the patient 300. In some examples, to removably secure the guide block 240 to the radius bone 310, a surgeon may use k-wires 360A, 360B, 360C that are placed through the openings 242 of the guide block 240. When the guide block 240 is secured to the radius bone 310, the distal radius guide may be positioned according to the proper positioning for testing as described above.

A surgeon may then prepare the distal surface of the radius bone 310 with the aid of the reaming guide 222 while the guide block 240 is removably secured to the radius bone 310. If the distal radius guide is positioned as illustrated in FIG. 3A, the surgeon may remove the bolt 210, remove the distal radius guide 220, rotate the distal radius guide 220 a half-revolution (e.g., 180°), place the distal radius guide 220 back on the resection instrument, and secure the bolt 210 to the resection instrument 200. As such, the reaming guide 222 is then in position relative to the distal surface of the radius bone 310 to guide a reamer. The surgeon may then use a reamer (e.g., a reamer corresponding to the selected distal radius guide 220 size) with the reaming guide 222 to prepare the distal surface of the radius bone 310. The distal surface of the radius bone 310 is prepared, for example, when the entire reamed surface is below the cartilage on the distal surface.

In some instances, the surgeon may adjust the depth control instrument 230 of the resection instrument 200 to incrementally increase the depth of the reamer so that the reamed surface is below the cartilage. For example, the surgeon may begin reaming with the depth control instrument 230 set just above the "0 mm" indication and find that the reamed surface is above the cartilage. The surgeon may then adjust the knob 232 to lower the distal radius guide 220 towards the guide block 240 to the "2 mm" indication, continue reaming, and find that the reamed surface is below the cartilage. In this way, the distal surface of the radius bone 310 is prepared. In some examples, the maximum reaming depth is 4 mm (e.g., the maximum indication that the depth control instrument 230 can be adjusted to is a "4 mm" indication).

The surgeon may then rotate the distal radius guide 220 a half-revolution again by removing the bolt 210 so that the trial socket 224 is in position relative to the radius bone 310 (e.g., the orientation illustrated in FIG. 3A). The example method may then include aligning a capitate implant (e.g., the capitate implant 110) based on the trial socket 224 while the guide block 240 is removably secured to the radius bone 310. For example, a surgeon may select a trial capitate implant 350 that replicates a capitate implant 110 and position the trial capitate implant 350 such that its stem is in the hole created in the capitate bone 332. Once the trial capitate implant 350 is positioned, the surgeon may test the range of motion of the hand of the patient 300 as the trial capitate implant 350 interfaces with the trial socket 224 of the distal radius guide 220 of the resection instrument 200. The surgeon may adjust the trial capitate implant 350 orientation to determine the optimal alignment that enables a suitable range of motion.

Once the trial capitate implant 350 is in its optimal alignment, the surgeon may create an offset hole in the capitate bone 332. The offset hole enables a capitate implant 110 to be positioned exactly how the trial capitate implant 350 is positioned. To create the offset hole, the surgeon may drill a k-wire through the trial capitate implant 350 and advance it under power into the capitate bone 332. The offset hole is adjacent and integral with the hole created in the capitate bone 332 after preparing the surface of the capitate bone 332.

Figure 3B:
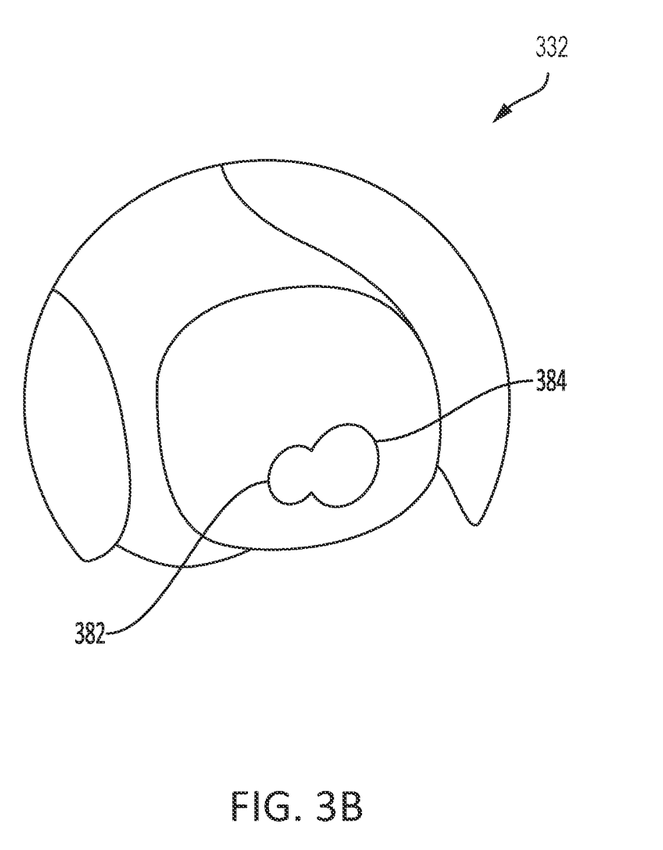
FIG. 3B illustrates a magnified view of the capitate bone of FIG. 3A having an example offset hole integral with a capitate hole, according to an aspect of the present disclosure.

FIG. 3B illustrates a magnified view of the capitate bone 332 of the patient 300 with an example offset hole 382 integral with a capitate hole 384, according to an aspect of the present disclosure. Accordingly, when a capitate implant 110 having a stem 114 with a protrusion 140 extending along at least a portion of its length is positioned in the capitate bone 332, the stem 114 is positioned so that the protrusion 140 is within the offset hole 382. Thus, by aligning the protrusion 140 within the offset hole 382, the capitate implant 110 is positioned into the capitate bone 332 exactly how the trial capitate implant 350 was positioned. Since the trial capitate implant 350 was determined to be to be in an alignment that enables a suitable range of motion for the patient 300, the inserted capitate implant 110 is therefore placed in the same suitable alignment. Accordingly, the capitate implant 110 may be aligned based on the trial capitate implant 350 and the trial socket 224.

Additionally, the protrusion 140 within the offset hole 382 prevents the capitate implant 110 from rotating and thus helps eliminate the need for a second stem on the capitate implant 110 that would otherwise maintain the positioning of the capitate implant 110. Eliminating the second stem helps reduce the material stress, as described above.

After the alignment for the capitate implant 110 is determined, the surgeon may remove the trial capitate implant 350 from the capitate bone 332. The surgeon may also remove the bolt 210, the distal radius guide 220, and the depth control instrument 230 from the guide block 240. Then, the surgeon may secure a capitate implant 110 to the capitate bone 332 such that the stem 114 of the capitate implant 110 is inserted within the capitate hole 384 created in the capitate bone 332. For example, the surgeon may inject bone cement into the capitate hole 384 and the offset hole 382 and then insert the stem 114 of the capitate implant 110 into the holes 382 and 384. The capitate implant 110 may be held in place until the cement sets.

Figure 4:
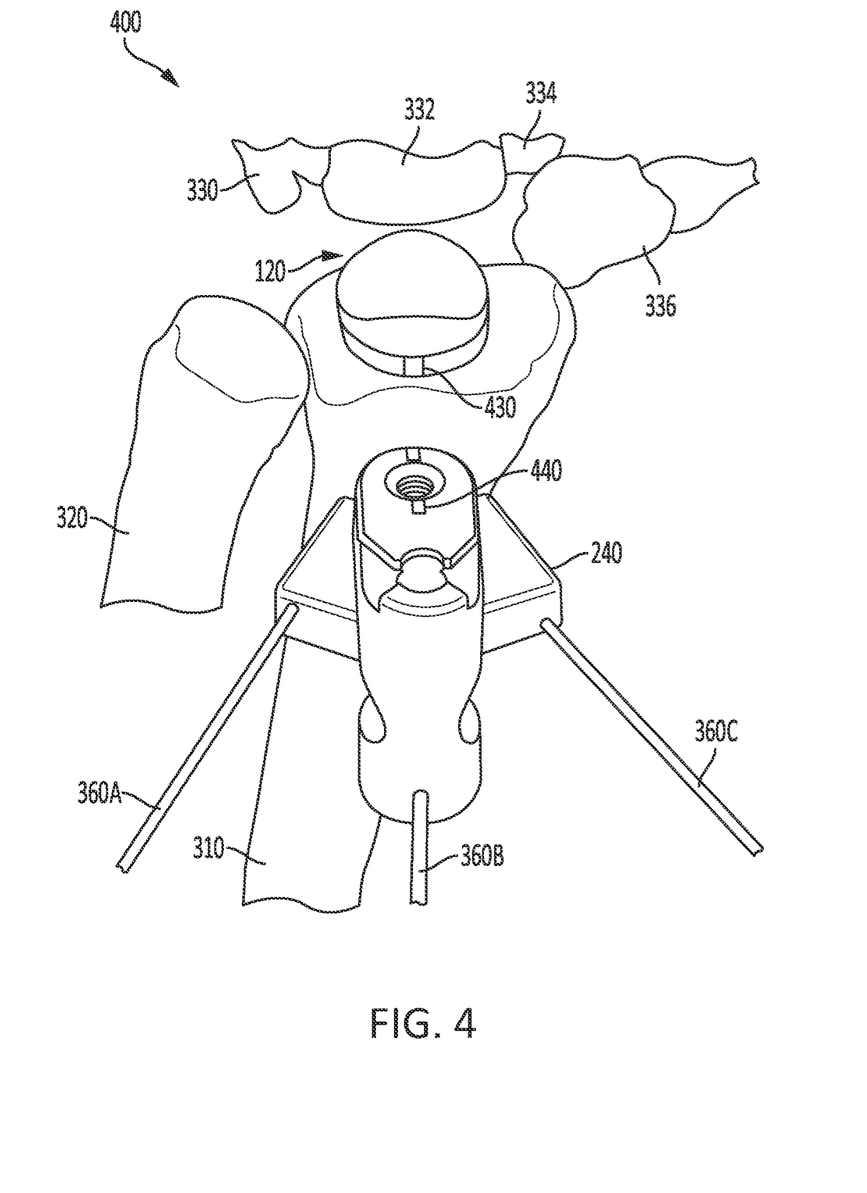
FIG. 4 illustrates an example patient with a properly aligned radial implant, according to an aspect of the present disclosure.

While the guide block 240 is still secured to the radius bone 310, the surgeon may then secure the radial implant 120 to the radius bone 310. For instance, the surgeon may inject bone cement into the holes created in the radius bone 310 and then insert the stem 128 and posts 126A, 126B into the holes. While the cement is setting, the surgeon may align the radial implant 120. FIG. 4 illustrates an example patient 400 with a properly aligned radial implant 120, according to an aspect of the present disclosure. For example, the radial implant 120 may include an alignment mark 430 and the guide block 240 may include one or more alignment marks 440. A surgeon may align the radial implant 120 by aligning the alignment mark 430 on the radial implant 120 with the alignment mark 440 on the guide block 440. Once aligned, the surgeon may secure the radial implant 120 to the radius bone 310 by letting the cement set. The surgeon may then remove the guide block 240 from the radius bone 310.

Figure 5:
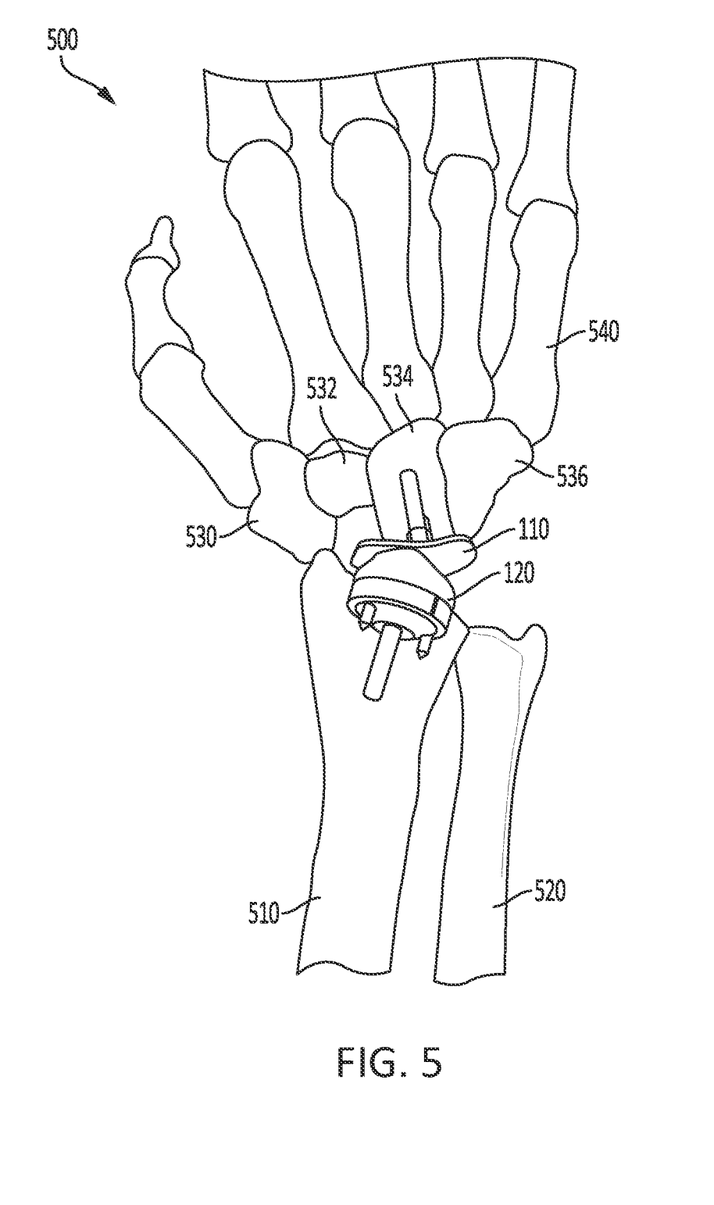
FIG. 5 illustrates an example wrist joint after a wrist arthroplasty, according to one aspect of the present disclosure.

FIG. 5 illustrates an example wrist joint 500 after a wrist arthroplasty, according to one aspect of the present disclosure. Whereas the preceding FIGS. 3A, 3B, and 4 illustrated a left wrist joint, FIG. 5 illustrates a right wrist joint, and thus the anatomy is a mirror image. For context, the wrist joint 500 includes a radius bone 510, an ulna bone 520, a trapezium bone 530, a trapezoid bone 532, a capitate bone 534, a hamate bone 536, and the five metacarpals 540 (only one of which is indicated). An example capitate implant 110 is secured within the capitate bone 534 and an example radial implant 120 is secured within the radius bone 510.

Without further elaboration, it is believed that one skilled in the art can use the preceding description to utilize the claimed inventions to their fullest extent. The examples and embodiments disclosed herein are to be construed as merely illustrative and not a limitation of the scope of the present disclosure in any way. It will be apparent to those having skill in the art that changes may be made to the details of the above-described embodiments without departing from the underlying principles discussed. In other words, various modifications and improvements of the embodiments specifically disclosed in the description above are within the scope of the appended claims. For example, any suitable combination of features of the various embodiments described is contemplated.

The invention claimed is:

1. A wrist arthroplasty system comprising:
    a capitate implant including a capitate stem extending from a carpal surface of a head portion, wherein the head portion includes a convex surface opposite the carpal surface;
    a radial implant including:
        a base component,
        a radial stem extending from a first side of the base component, and
        a socket extending from a second side of the base component opposite the first side, wherein the socket includes two lips forming a concave opening adapted to interface with the convex surface of the capitate implant; and
    a resection instrument including:
        a distal radius guide including a trial socket formed integrally with a reaming guide, wherein the trial socket is configured to substantially replicate the socket of the radial implant, and wherein the reaming guide includes an opening sized according to the trial socket,
        a guide block including a plurality of holes each adapted respectively to receive a fixture instrument, wherein the guide block is configured to receive a depth control instrument, and
        the depth control instrument including an adjustment knob, wherein the depth control instrument is configured to removably engage with the guide block such that, when engaged, rotating the adjustment knob causes the depth control instrument to translate relative to the guide block.

2. The system of claim 1, wherein the convex surface of the capitate implant includes a curvature adapted to replicate a surface of a lunate facet nearest a distal surface of a radius bone.

3. The system of claim 1, wherein the capitate implant includes a cobalt chromium alloy.

4. The system of claim 1, wherein the radial implant includes a titanium alloy.

5. The system of claim 1, wherein the socket includes high molecular weight polyethylene.

6. The system of claim 1, wherein the distal radius guide is removably secured to the guide block.

7. The system of claim 1, wherein the resection instrument includes a set of distal radius guides, wherein each respective distal radius guide of the set of distal radius guides includes a trial socket of a different size.

8. The system of claim 7, further comprising a set of reamers, wherein each respective reamer of the set of reamers corresponds to a respective distal radius guide of the set of distal radius guides.

9. The system of claim 1, wherein the depth control instrument includes a threaded leg and an indicator leg including a plurality of indicators, and wherein the threaded leg is configured to engage with the guide block such that rotating the adjustment knob causes the depth control instrument to translate relative to the guide block.

* * * * *